United States Patent [19]

Gard

[11] Patent Number: 5,220,589
[45] Date of Patent: Jun. 15, 1993

[54] CORRECTION CIRCUIT FOR A FLOATING-POINT AMPLIFIER

[75] Inventor: Michael F. Gard, New Berlin, Wis.

[73] Assignee: General Electric Company, Milwaukee, Wis.

[21] Appl. No.: 732,381

[22] Filed: Jul. 18, 1991

[51] Int. Cl.⁵ .............................................. H05G 1/60
[52] U.S. Cl. ........................................ 378/19; 378/4
[58] Field of Search .............................. 378/4, 19, 901

[56] References Cited

U.S. PATENT DOCUMENTS

| | | | |
|---|---|---|---|
| 4,068,306 | 1/1978 | Chen et al. | 378/901 |
| 4,278,889 | 7/1981 | Erker | 378/19 |
| 4,815,118 | 3/1989 | Acharya et al. | 378/19 |

Primary Examiner—Craig E. Church
Attorney, Agent, or Firm—Quarles & Brady

[57] ABSTRACT

A medical imaging system has a source of X-rays and a detector which produces an electrical signal in response to X-rays from said source. A circuit amplifies the electrical signal by a gain factor that varies in response to a number received from a gain control circuit. A converter transforms an analog output signal from the amplifier into digital data. An error compensation circuit stores an offset correction value and a gain correction value for each value of the number from the gain control circuit. A pair of correction values is selected based on the gain of the amplifier for a given item of digital data. The selected offset correction value is summed with the item of digital data and the result is multiplied by the selected gain correction value. A circuit is provided to numerically integrate the corrected data.

17 Claims, 3 Drawing Sheets

CORRECTION CIRCUIT FOR A FLOATING-POINT AMPLIFIER

BACKGROUND OF THE INVENTION

The present invention relates to mechanisms for providing offset and gain correction of the output from a floating-point amplifier; and more particularly, to such a correction mechanism specifically adapted for use in amplifier circuits of computed tomography (CT) imaging apparatus.

In a computed tomography system, an X-ray source projects a fan beam which is collimated to lie within an X-Y plane of a Cartesian coordinate system, termed the "imaging plane". The beam is transmitted through an object to be imaged and then impinges upon an X-ray detector array oriented within the imaging plane. The detector array is formed of a plurality of individual elements with each element measuring the intensity of the radiation transmitted from the source to that element. The intensity of the transmitted radiation is dependent upon the attenuation of the X-ray beam by the object.

The X-ray source and detector array in a common CT system are rotated on a gantry within the imaging plane and around the imaged object so that the angle at which the fan beam intersects the object constantly changes. As the gantry rotates, a number of X-ray projections forming a projection set are acquired. Each projection is made up of the intensity signals from the detector elements as they travel over a small angle of gantry rotation centered about a projection angle.

The acquired tomographic projection sets typically are stored in numerical form for computer processing to reconstruct a slice image according to array processing algorithms known in the art. A set of CT projections may be transformed directly into an image by means of a fan beam reconstruction technique or the intensity data of the projection may be sorted into parallel beams and reconstructed according to parallel beam reconstruction techniques. The reconstructed tomographic images then are displayed on a video monitor or converted into a film record by means of a computer controlled camera.

In conventional CT systems, the signal from the detector array is amplified and digitized in a unit referred to as a data acquisition system (DAS). The data acquisition system is composed of two primary components: a floating-point amplifier and an analog to digital converter. Both of these devices may introduce errors into the signal from the detector array. For example, the DAS amplifier may introduce a signal offset which varies with the different gain settings of the amplifier, as shown in FIG. 1A. This figure graphically depicts the amplifier transfer function, i.e. input versus output voltage levels, for two gain settings $G_1$ and $G_2$ of the floating-point amplifier in the DAS. Each of these different gain levels has a separate offset error which corresponds to the amount that the transfer function is displaced along the vertical axis from the origin. A conventional technique for compensating offset errors collects data when the X-ray beam is off and the detector signal is relatively small. As a result, the offset error data is acquired at the highest possible gain level of the amplifier (e.g gain $G_1$) and the resultant offset value is used thereafter to compensate not only signals produced by the amplifier at this gain level but at all other gain levels. In general, the offset at the other gains is not the same and a single offset correction actually introduces errors by shifting the transfer function of other levels (e.g. $G_2$) a constant amount as shown in FIG. 1B. In this case, the offset correction has been set to compensate for the amplifier errors at a gain $G_1$, but has not eliminated the offset error at gain $G_2$.

Likewise, each gain level of the programmable amplifier can have a unique departure from its ideal transfer function due to gain error. Each gain level $G_1$ and $G_2$ in the example provide different deviations from their ideal transfer functions $I_1$ and $I_2$ respectively, as shown in FIG. 2A in the absence of offset errors. Previously, a single gain correction factor was determined from the error at the highest gain level. This single correction factor Gc compensates for the error at $G_2$ of the floating-point amplifier to bring its transfer function into coincidence with its ideal $I_2$ as shown in FIG. 2B. However, the single gain correction factor can actually increase the error at another gain setting ($G_1$) as illustrated.

Furthermore, previous CT systems used the array processor to reconstruct the image from the set of projections. The array processor also was saddled with the task of performing the error correction as well. This degraded the performance of the array processor as it required continual interruption of the image reconstruction to apply offset and error correction to the incoming projection data. Using the array processor in this manner increased the time required between data collection and image presentation.

SUMMARY OF THE INVENTION

Although the present invention is being described in the context of a medical imaging system, it has broader application to error compensation in a wide variety of data processing apparatus.

A medical imaging system that incorporates the instant error compensation system has a source of X-radiation and a detector which produces an electrical signal in response to the X-radiation received from said source. A variable gain amplifier is coupled to the detector to amplify the signal. The gain factor of the amplifier varies in response to a numerical value from a gain control circuit that determines the gain based upon the magnitude of the electrical signal. An analog-to-digital converter transforms the analog output from the variable gain amplifier into digital data. In a typical imaging apparatus, each item of the digital data is represented by an exponent and a mantissa, where the exponent is related to the numerical value from the gain control circuit. Both the amplifier and the converter can introduce offset and gain errors into the data during their processing operations, for example.

The present invention provides an error compensation circuit to correct for the errors from non-ideal data processing. A memory stores a series of correction factors. When an item of data is to be corrected, one of the stored correction factors is selected in response to the value of the data exponent. The selected correction factor is combined with the data mantissa to compensate for errors in the mantissa.

In an embodiment for the imaging system, offset and gain correction factors are stored in the memory for each possible value of the exponent. The selected offset correction factor is summed with the mantissa and the result is multiplied by the gain correction factor selected by the exponent value. The order of the arithmetic operations can be reversed. Other components can be incorporated into the basic correction circuit for data compression and numerical integration of the output from the image detector, as will be described.

A general object of the present invention is to provide a system which compensates for errors in a data converting and processing apparatus, such as gain and offset errors from a variable gain amplifier.

Another object of the present invention is to provide an data error compensation system which has separate correction factors associated with different gain settings of the amplifier.

Additional features can be included with the basic error compensation in which case a further object is to provide a data compression device in conjunction with the error compensation system. Yet another object is to incorporate a numerical integrator for the data being handled by the error compensation system.

DETAILED DESCRIPTION OF THE INVENTION

Figure 1A:
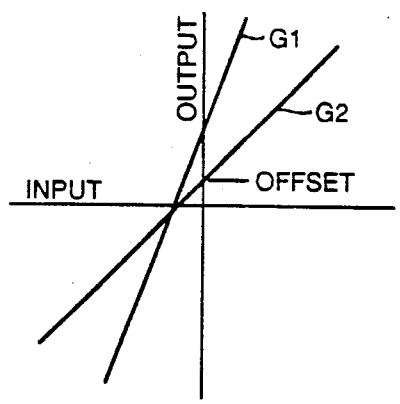
FIGS. 1A and 1B graphically illustrate signal offset errors in the input to output transfer function of a data acquisition system within a CT apparatus.
Figure 1B:
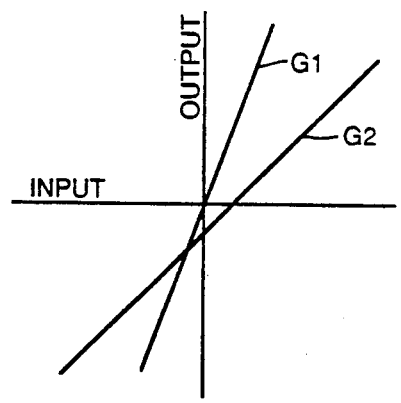
Figure 2A:
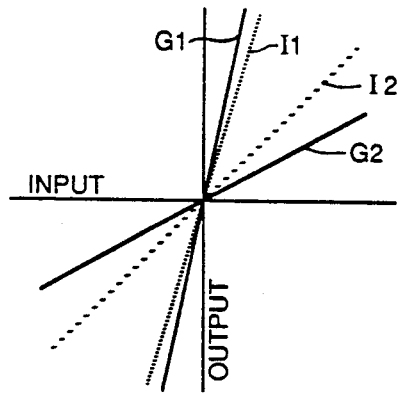
FIGS. 2A and 2B illustrate gain errors introduced by the data acquisition system.
Figure 2B:
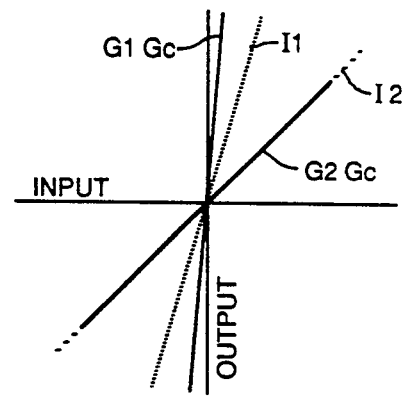
Figure 3:
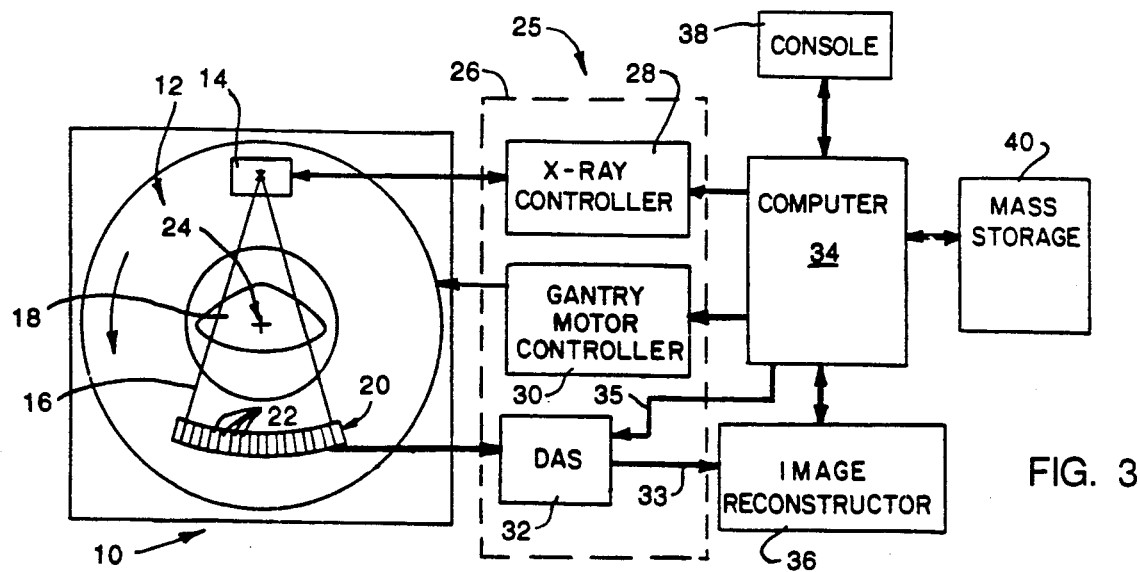
FIG. 3 is a block schematic diagram of a CT apparatus.

With initial reference to FIG. 3, a computed tomography (CT) imaging system 10 includes a gantry 12 representative of a "third generation" CT scanner. The gantry 12 includes an X-ray source 14 oriented to project a fan beam of X-rays 16 through imaged object 18 to detector array 20. The detector array 20 is formed by a number of detector elements 22 which together detect a projected image resulting from the transmission of X-rays through the imaged object 18. The gantry 12 rotates about a center of rotation 24 located within the imaged object 18.

A control mechanism 25 of the CT system 10 has gantry associated control modules 26 which include an X-ray controller 28 which provides power and timing signals to the X-ray source 14, a gantry motor controller 30 that controls the rotational speed and position of the gantry 12, and a data acquisition system (DAS) 32 which samples projection data from detector elements 22 and converts the data to digital words for later computer processing.

The X-ray controller 28 and the gantry motor controller 30 are connected to a computer 34 such as a Data General Eclipse MV/7800C general purpose minicomputer. The computer 34 also provides processing data and control signals to DAS 32 via a set of control buses 35. The DAS 32 is connected to an image reconstructor 36 which receives sampled and digitized projection data from the DAS 32 via data bus 33 and performs high speed image reconstruction according to methods known in the art. For example, the image reconstructor 36 may be an array processor such as one manufactured by Star Technologies.

The computer 34 receives commands and scanning parameters via an operator console 38 that has a cathode ray tube display and keyboard which allow the operator to enter parameters for the scan and observe the reconstructed image and other information from the computer 34. A mass storage device 40 provides a means for storing operating programs for the CT imaging system, as well as image data for future reference by the operator.

Figure 4:
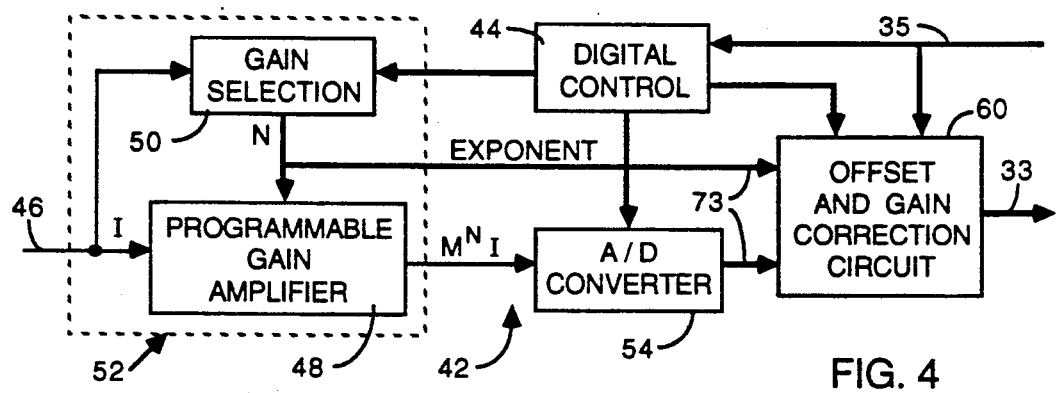
FIG. 4 is a block diagram of a portion of the digital acquisition system in FIG. 3.

The data acquisition system 32 in the preferred embodiment has a separate circuit which filters, amplifies, digitizes and otherwise conditions the signal from each detector element 22. However, one or a small number of such processing circuits can be provided with the individual signals from the detector elements being time division multiplexed into that circuit, as was done in previous systems. FIG. 4 illustrates one of these signal processing circuits 42 in DAS 32. A signal line 46 from the detector element is connected to the input of a programmable gain amplifier 48 and a gain selection circuit 50 which form a floating-point amplifier 52. In general, the input (I) to output (O) transfer function of the floating-point amplifier 52 is of the form $O=M^N I$, where N is an integer number (e.g. 0, 1, 2, 3, etc.) whose value, for example, increases for smaller levels of analog input signals from the detector element 22, and where M is a selected integer power of two (e.g. 8). The floating-point amplifier 52 functions so that N is dynamically selected as a function of the magnitude of its analog input signal and the output of amplifier 48 is between defined minimum and maximum values, thereby limiting, by the size of M, the number of zero-valued most significant bits delivered by the A/D converter 54 for subsequent image analysis. This insures that the projection resolution for the amplifier and converter combination will be relatively independent of the input signal value, a desired characteristic for a CT data acquisition system. The floating point amplifier also insures that large magnitude detector signals do not overload the circuitry.

The output of the analog to digital converter 54 is typically a fourteen bit digital number. Therefore, each item of projection data is a sixteen bit number having a data format consisting of a two bit exponent N from the gain selection circuit 50 and a fourteen bit mantissa from the A/D converter 54. The exponent represents the amount of gain applied to the signal by the floating-point amplifier 52. The digital output from the A/D converter 54 is fed to a gain and offset correction circuit 60 which compensates for the errors introduced by the floating-point amplifier 52 and the analog to digital converter 54. The correction circuit is a special arithmetic unit which can perform view compression and signal integration under certain circumstances, as will be described. The components 50, 54 and 60 of the DAS processing circuit 42 are connected to a digital control 44 which interfaces with the system computer 34.

Figure 5:
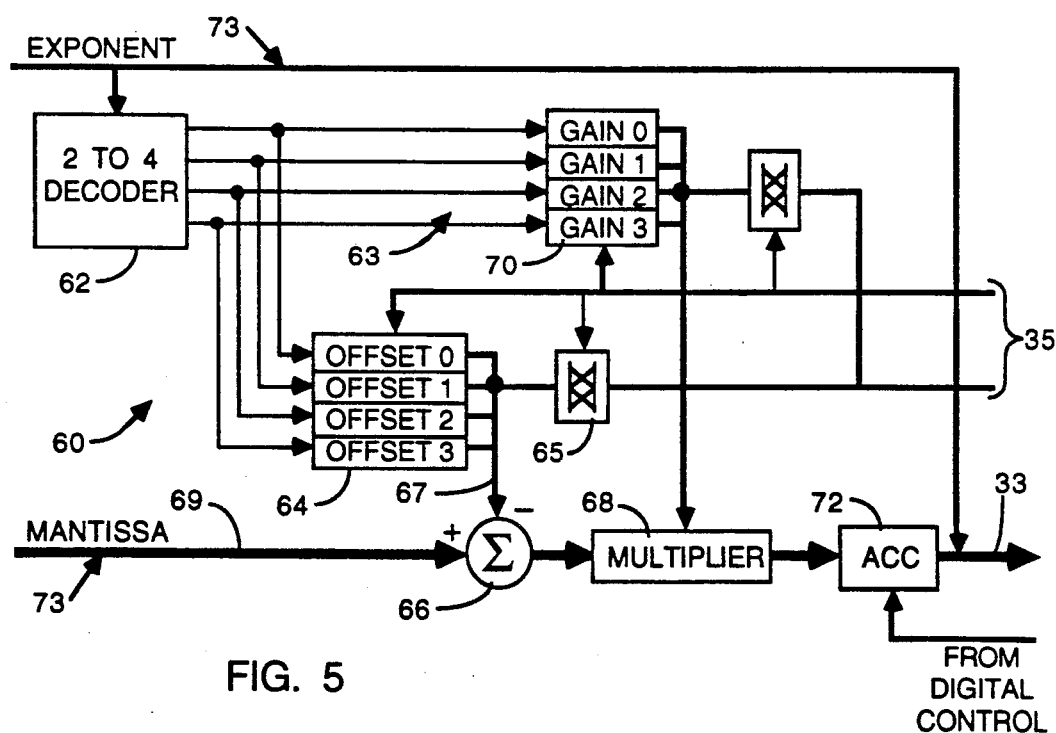
FIG. 5 is one embodiment of an offset and gain correction circuit shown in FIG. 4.

One embodiment of the offset and gain correction circuit 60 is shown in FIG. 5. The exponent portion of the data is received from the gain selection circuit 50 by a two to four decoder 62. The exponent N is represented by two bits, thereby defining four different gain factors. Decoder 62 responds to the two bit exponent by activating one of four output lines 63 connected to a quartet of offset value registers 64. Each register 64 contains the appropriate offset compensation value for one of the four gain levels used by the floating-point amplifier 52. Each value is a signed digital number which provides the proper compensation for the offset error produced at that gain level.

The offset compensation values are determined during a configuration phase of the CT system operation. At that time, a known input signal level is applied to the input line 46 of the floating-point amplifier 52 and the programmable gain amplifier 48 is sequentially set to each of the gain factors by the gain selection circuit 50 responding to commands from computer 34 sent to digital control 44. The output of the DAS 32 at each gain setting is fed by the image reconstructor 36 to the computer 34 which compares the actual output value to the ideal value to determine the signal offset. From the signal offset at each gain setting, a group of correction values is determined. The group of offset correction values is transferred from the computer 34 to the appropriate registers 64 via control bus 35 and data buffer 65.

During acquisition of projection data, the two to four decoder 62 enables one of the offset registers 64 in response to the value of the exponent. The offset correction value stored in the enabled offset register 64 is applied via a common set of output lines 67 to one input of a summation circuit 66. The mantissa of the projection data from the analog to digital converter 54 is coupled in parallel to another input 69 of the summation circuit 66. The term "summation circuit" as used herein is defined as including circuitry which adds or subtracts the two input values. The particular implementation of the summation circuit in FIG. 5 is a circuit that subtracts the offset correction value from the mantissa of the projection data. The offset correction value from registers 64 is combined with the mantissa to compensate for the offset error produced in the floating-point amplifier 52 and A/D converter 54. The partially compensated projection data are applied to one input of a multiplier 68.

The output lines 63 from the two to four decoder 62 are applied also to a set of four gain correction registers 70. These registers 70 store correction values for the gain error of the floating-point amplifier 52 at the different programmable gain levels. The gain correction values are determined by a similar process to that employed to set the offset correction values, as described above. During acquisition of projection data, the output from the decoder 62 enables one of the gain correction registers 70 to supply its stored value to another input of the multiplier 68. The multiplier 68 uses the gain correction value to operate on the output of the summation circuit 66 to produce a resultant digital value which has been compensated for the gain and offset errors introduced into the projection data by the data acquisition system 32.

Although the circuit in FIG. 5 has been described in terms of digitized projection data flowing in a parallel data format through the summation circuit 66 and multiplier 68, a serial data transmission format may be used. A serial format can simplify the circuitry of the multiplier 68.

The output of multiplier 68 can be fed directly to the image reconstructor 36 in FIG. 3. Alternatively, the present gain and offset correction circuit 60 can perform view compression by averaging data from the detector element produced at several (e.g. four) projection angles to reduce the amount of image data to be processed by the image reconstructor 36. In this case, shown in FIG. 5, the output from multiplier 68 is applied to the input of an accumulator (ACC) 72 which combines several samples of projection data from the detector element to produce a single data sample for transmission to the image reconstructor 36. The accumulator 72 is operated by signals from the digital control 44. In either case, once the data has been transmitted to the image reconstructor 36, conventional image reconstruction techniques are utilized to formulate the image and present it to the system operator.

Thus, the present offset and gain correction circuit 60 compensates for errors introduced by the CT digital acquisition system 32 without intervention by the array processor in the image reconstructor 36. This allows the array processor to be used to its full potential in image reconstruction and eliminates delays previously required for error compensation.

The embodiment of the DAS 32 described thus far digitizes the output from a detector element 22 to produce one data sample per projection. The intensity of the X-rays striking the detector element 22 typically varies instantaneously during each projection. Thus, a single data sample of the detector element output may not accurately represent the true intensity of the impinging radiation during the duration of the protection period. A more accurate representation of the X-ray intensity can be obtained by integrating the output of each detector element 22 over the projection period. Although the detector signals can be integrated by analog integrators, analog integrators have inaccuracies due to temperature variation and component non-idealities, in addition to requiring a relatively long zeroing time.

Figure 6:
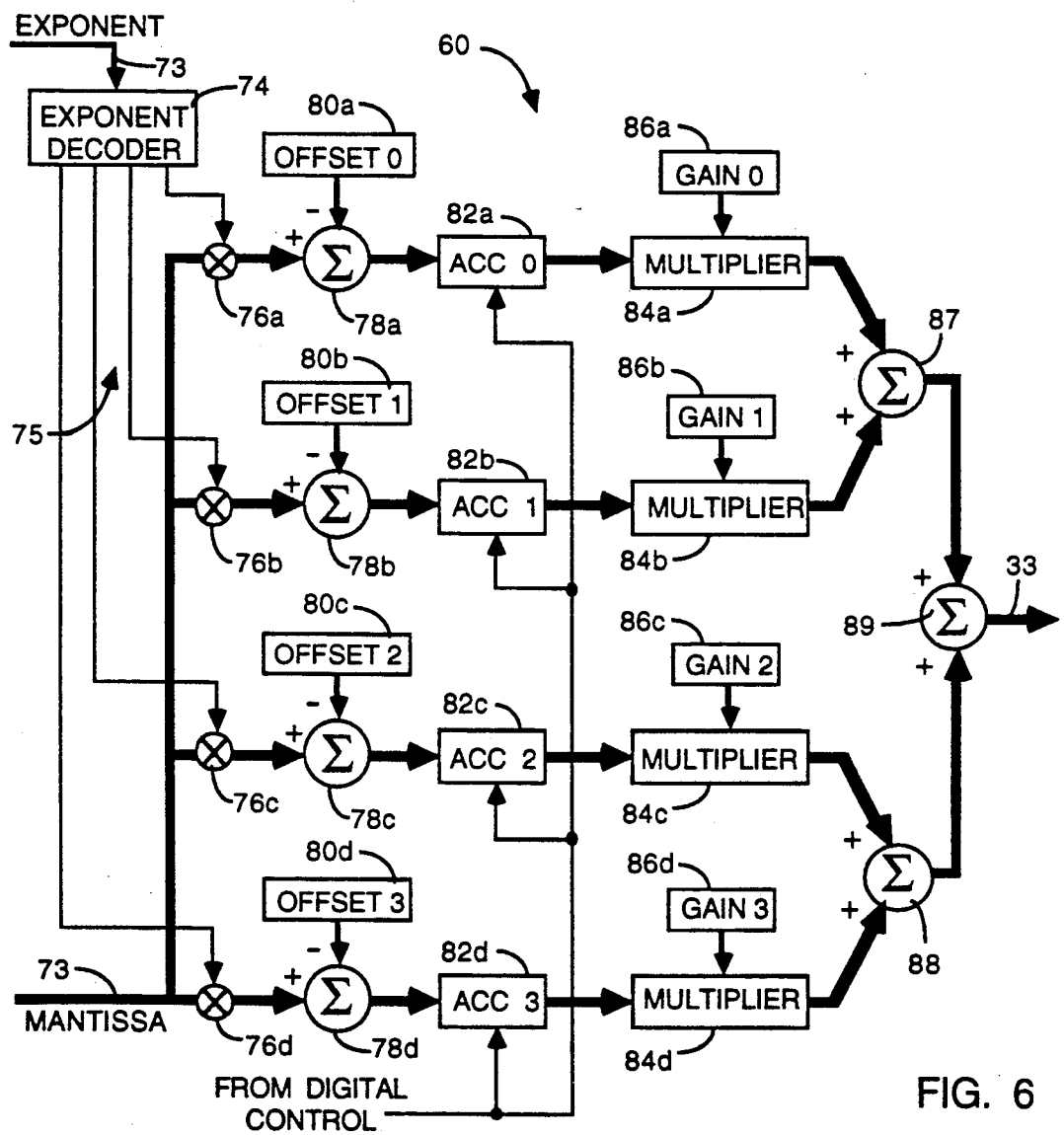
FIG. 6 is an alternative embodiment for the offset and gain correction circuit.

FIG. 6 shows an alternative embodiment of the offset and gain correction circuit 60 that includes numerical integration of the digitized data from the A/D converter 54, which does not possess many of the disadvantages associated with analog integrators. In this version, the A/D converter 54 is clocked several times during each projection period to produce a series of digital data samples for integrating. Typically, sixteen or more data samples are produced from the detector element signal during a single CT projection period. As the signal from the detector element varies instantaneously during this period, the exponent as well as the mantissa of the data samples may vary.

The second embodiment of the offset gain and correction circuit 60 has four separate parallel data paths A, B, C and D with each path processing the data samples amplified by a different gain factor of the programmable gain amplifier 48. Some of the correction circuit components are designated by a numeral followed by a letter a, b, c or d corresponding to the path in which the component is located.

The exponent (N) of each data sample, which indicates the applied gain, is coupled via input port 73 to a two to four exponent decoder 74 that responds to the value of the two bit exponent by sending an enable signal onto one of four output lines 75. The output lines 75 are connected to four sets of data gates 76a–d having a parallel data input coupled via input port 73 to the output of the A/D converter 54 for receiving the mantissa of the projection data. The sets of data gates 76a–d, when enabled by the signal on the associated output line 75 from decoder 74, couple the mantissa from the A/D converter 54 to the inputs of a corresponding summation circuit 78a, b, c or d. Another input of each summation circuit is connected to the output of a separate data register 80a–d which stores an offset correction value for one of the amplifier gain factors. The output of the summation circuit 78a–d is a multi-bit digital number which has been corrected for the offset errors introduced previously into the projection data.

The output of the summation circuit 78a-d in each branch A, B, C and D is connected to the input of a separate accumulator (ACC) 82a-d. As each data sample is received by the correction circuit 60, the exponent decoder 74 enables the data gate 76a, b, c or d in the path for data samples amplified by the corresponding gain. The associated summation circuit 78a-d applies the appropriate offset correction value to the data sample. Each accumulator 82a-d totals the mantissas of the data samples from a given projection which have the same exponent value.

At the completion of the projection period, the contents of the four accumulators 82a-d are read simultaneously in response to a signal from the digital control 44 and applied to the input of separate multipliers 84a-d for the associated data path A-D. Another input of each of the multipliers 84a-d receives the output from a separate gain correction value register 86a-d, respectively. The outputs from the accumulators 82a-d are multiplied by the corresponding gain correction value to produce a product which has been corrected for gain errors introduced by previous components of the digital acquisition system 32. The multipliers 84a-d also normalize the accumulated data so that the data from each path A, B, C and D can be summed to provide an approximation of the integrated X-ray intensity.

The multi-bit digital outputs from the multipliers 84a-d are arithmetically combined by three summation circuits 87, 88 and 89 to produce an integrated projection value for the detector element. This sample of the projection data is sent via data bus 33 to the image reconstructor 36. Thereafter, the accumulators 82a-d are reset to zero in order to process data for the next projection. As the data for each picture element is normalized by the multipliers, the exponent is not sent to the image reconstructor 36 in this embodiment.

The offset and gain correction values for the second embodiment are determined by the computer 34 and stored in the corresponding registers 80a-d and 86a-d in a similar manner to that used with respect to the embodiment shown in FIG. 5. To simplify FIG. 6, the necessary control data and signal lines and buffers for this storage have not been shown.

I claim:

1. A computed tomographic imaging system comprising:
    a source of radiation;
    an array of detector elements each of which produces an electrical signal in response to radiation received from said source;
    means for rotating said source and said array about an object being imaged to acquire electrical signals from the detector elements at a plurality of projections about the object;
    a circuit for amplifying and digitizing the electrical signals from the detector elements to produce a plurality of digital data samples of the signal from each detector element at each projection; and
    means for separately integrating the plurality of digital data samples acquired from the signal of each detector element at each projection.

2. The computed tomographic imaging system as recited in claim 1 wherein said means for separately integrating comprises an accumulator which produces a sum of digital data samples from a detector element, the sum being reset to zero upon movement of the detector element to another projection position.

3. The computed tomographic imaging system as recited in claim 1 further comprising an error compensation circuit for combining a correction value with the digital data samples, the correction value being selected from a plurality of such values in response to a gain factor of said circuit for amplifying and digitizing.

4. The computed tomographic imaging system as recited in claim 1 wherein said circuit for amplifying and digitizing comprises:
    a variable gain amplifier coupled to said array and having a gain level that varies in response to a number received at a control input;
    means for determining a value for the number in response to the magnitude of the electrical signal received from the array, and applying the number to the control input of said variable gain amplifier; and
    a converter which transforms an analog output from said variable gain amplifier into digital data samples.

5. The computed tomographic imaging system as recited in claim 4 further comprising an error compensation circuit comprising:
    a memory for storing a plurality of correction values;
    means for selecting a correction value from said memory in response to the number from said means for determining; and
    means for arithmetically combining the selected correction value received from said memory with a digital data sample.

6. The computed tomographic imaging system as recited in claim 4 further comprising an error compensation circuit comprising:
    a plurality of data paths, each of which includes a means for storing a correction value, an arithmetic means for combining the stored correction value received from said means for storing with a digital data sample, and a data buffer for selectively coupling digital data samples from said converter to the arithmetic means when enabled by a control signal; and
    means for producing a control signal to selectively enable the data buffer in one of said data paths in response to the number from said means for determining; and
    a plurality of accumulators each connected in series with elements of one of the data paths.

7. The medical imaging system as recited in claim 6 further comprising means for combining data from each data path.

8. A medical imaging system comprising:
    a source of radiation;
    a detector which produces an electrical signal having a magnitude that corresponds to radiation received by said detector from said source;
    a variable gain amplifier coupled to said detector and having a gain level that varies in response to a number at a control input;
    means for determining a value for the number in response to the magnitude of the electrical signal and applying the number to the control input of said variable gain amplifier;
    a converter which transforms an analog output from said variable gain amplifier into digital data; and
    an error compensation circuit for combining a correction value with the digital data received from said converter, the correction value being selected from a plurality of such values in response to the number received from said means for determining.

9. The medical imaging system as recited in claim 8 wherein said error compensation circuit comprises:
a plurality of data paths, each of which includes a means for storing a correction value, an arithmetic means for combining a correction value received from said means for storing with digital data, and a data buffer for selectively coupling the digital data from said converter to the arithmetic means when enabled by a control signal; and
means for producing a control signal to selectively enable the data buffer in one of said data paths in response to the number from said means for determining.

10. The medical imaging system as recited in claim 8 wherein said error compensation circuit comprises:
a memory for storing a plurality of correction values;
means for selecting a correction value from said memory in response to the number from said means for determining; and
means for arithmetically combining the selected correction value received from said memory with the digital data.

11. The medical imaging system as recited in claim 8 wherein said error compensation circuit comprises:
a memory for storing a plurality of transfer function offset correction values;
means for selecting a offset correction value from said memory in response to the number from said means for determining; and
a summation circuit for combining the selected offset correction value received from said memory with the digital data.

12. The medical imaging system as recited in claim 8 wherein said error compensation circuit comprises:
a memory for storing a plurality of signal gain correction values;
means for selecting a signal gain correction value from said memory in response to the number from said means for determining; and
means for multiplying the selected signal gain correction value received from said memory with the digital data.

13. The medical imaging system as recited in claim 8 wherein said error compensation circuit comprises:
a first memory for storing a plurality of transfer function offset correction values;
a second memory for storing a plurality of signal gain correction values;
means for selecting a offset correction value and a signal gain correction value from said first and second memories in response to the number from said means for determining;
a means for receiving the digital data from said converter;
a summation circuit for combining the selected offset correction value received from said first memory with digital data;
means for multiplying the selected signal gain correction value received from said second memory with digital data; and
means for connecting said summation circuit and said means for multiplying in series with said means for receiving the digital data.

14. The medical imaging system as recited in claim 8 further comprising a means for numerically integrating a plurality of digital data samples received from said error compensation circuit.

15. The medical imaging system as recited in claim 8 wherein said error compensation circuit comprises:
a plurality of data paths, each of which includes a data buffer for selectively coupling digital data from said converter to the data path, a first means for storing a transfer function offset correction value, a summation circuit for combining the offset correction value received from said first means for storing with digital data, a second means for storing a gain correction value, a means for multiplying the gain correction value received from said second means for storing with digital data, said summation circuit and said means for multiplying being connected in series with said data buffer; and
means for producing a control signal to selectively enable the data buffer in one of said data paths in response to the number from said means for determining.

16. The medical imaging system as recited in claim 15 further comprising means for combining data from each data path.

17. The medical imaging system as recited in claim 15 wherein each data path further comprises a means for numerically integrating a plurality of digital numbers connected in series with said summation circuit, said means for multiplying and said data buffer.

* * * * *